April 19, 1938.
R. ENGLE
CARNATION
Filed July 14, 1937
Plant Pat. 275
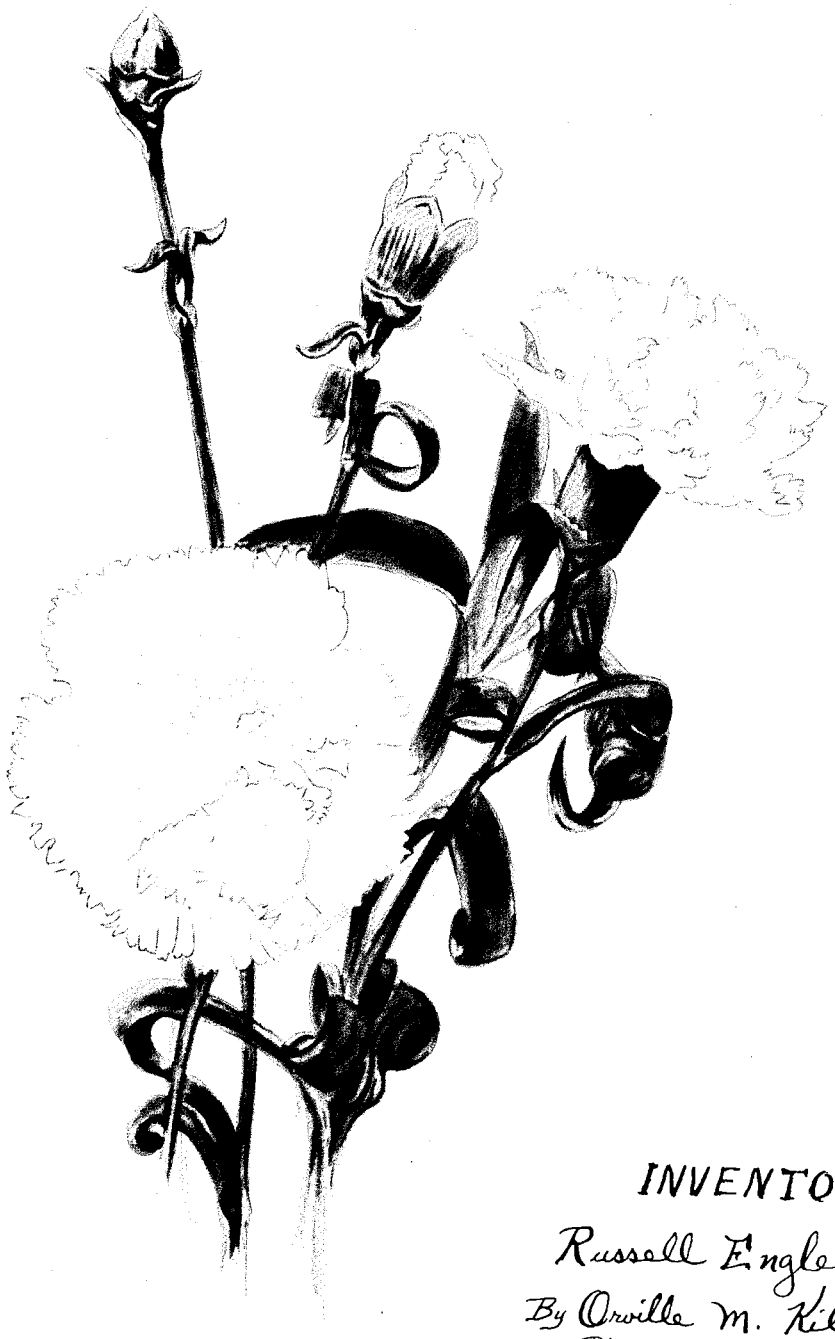
INVENTOR
Russell Engle
By Orville M. Kile
Plant Patent Agent Patented Apr. 19, 1938

Plant Pat. 275

UNITED STATES PATENT OFFICE

275

CARNATION

Russell Engle, Kokomo, Ind., assignor to Tom Knipe, Kokomo, Ind.

Application July 14, 1937, Serial No. 153,655

1 Claim. (Cl. 47—60)

My present invention relates to carnations usually known as the greenhouse forcing type and has particular reference to improvements in the novel color class. Its most outstanding characteristic in addition to color is the vigorous growth and ability to produce an unusually large number of blossoms. It produces many more blossoms than any carnation near its color and more than most varieties of whatever color.

This new variety was originated by crossing a red striped unnamed seedling with a dark pink unnamed seedling, the parentage being unknown in the case of both seedlings. This new variety has been asexually reproduced over a period of five years and its characteristics have persisted without change.

The accompanying illustrations show in approximately natural color and size in the original, a side view, a full front view, a tight bud, a partly opened bud, and some stems and foliage. Allowance must be made, however, for the fact that because of the difficulty in shading the artist cannot show the color as uniform or exact.

Following is a more detailed description of this new carnation variety. All color plate references are to Ridgway's Color Standards and Nomenclature.

*The plant*

*Growth habits.*—Makes good plants in the field and transplants easily. Very strong and vigorous; somewhat taller than the average variety, attaining a height of about 40 inches.

*Blooming habit.*—Comes into bloom early, blooms very freely and continuously.

*Foliage:*—

*Leaves.*—Very broad, the lower ones averaging ¾ inch in width. Length medium. Some of the leaves are somewhat curled but many are straight. Color is Dark Green (Plate XVIII), covered with gray bloom.

*Stems.*—Exceedingly strong and heavy. Straight but with large nodes. Very long. Color is Dark Green (Plate XVIII), covered with gray bloom.

*The flower*

*Bud.*—Slender and of rather uniform thickness. Moderately pointed at end.

*Bloom:*—

*Size.*—Under good greenhouse conditions it attains a size of about 2½ to 3½ inches in diameter.

*Petalage.*—45 to 50 petals (in June).

*Petals.*—Irregularly serrated, ruffled, rather flattened across top. Shank very long, comprising more than half the total length of petal.

*Color.*—The color in Ridgway's which approaches most nearly is Pale Rosolane Purple (Plate XXVI) with probably slightly more of a lavender or orchid tone but not as lavender as Rose Purple on the same plate.

*Calyx.*—Consists of a single tube 1½ inches long, divided into five lobes. Exceedingly strong and does not split. Color, Light Cress Green to Cress Green (Plate XXXI).

*Fragrance.*—Rather mild cinnamon fragrance.

*Reproductive organs*

*Pistils:*—

*Ovary.*—Large—about ½ inch long. Set into a pithy cup which is itself about ⅜ inch high, the total height when in position being about ¾ inch. The hard case of the ovary encloses many ovules.

*Styles.*—Set upon the top of the ovary are two (usually) styles 1¾ inches long. These are white and curled at the end. About half way up the style there appear two small stipule-like projections. Over-all length of entire pistil is about 2¼ inches.

*Stamens.*—Arising from the edge of the pithy cup are a few ragged and irregular stamens of varying lengths, some of which are topped by small yellowish anthers. None of these stamens extend more than about half as high as the styles.

Having thus disclosed my invention, I claim:

A new variety of carnation substantially as shown and described, characterized particularly by its freedom and continuity of blooming, its strong and vigorous growth resulting in long strong stems, its tough non-splitting calyx, its unusually broad leaves, and its large blossoms of a distinct color as shown.

RUSSELL ENGLE.